US00PP25990P2

(12) United States Plant Patent
Yates

(10) Patent No.: US PP25,990 P2
(45) Date of Patent: Oct. 13, 2015

(54) ***BEGONIA* PLANT NAMED 'TESSDARK'**

(50) Latin Name: ***Begonia* hybrid**
Varietal Denomination: TESSDARK

(71) Applicant: Frederic C. Yates, Congleton (GB)

(72) Inventor: Frederic C. Yates, Congleton (GB)

(73) Assignee: FLORENSIS BV,
Hendrik-Ido-Ambacht (NL)

( * ) Notice: Subject to any disclaimer, the term of this patent is extended or adjusted under 35 U.S.C. 154(b) by 39 days.

(21) Appl. No.: 13/999,943

(22) Filed: Apr. 7, 2014

(51) Int. Cl.
*A01H 5/02* (2006.01)

(52) U.S. Cl.
USPC ..... Plt./343

(58) Field of Classification Search
USPC ..... Plt./343
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of hybrid *Begonia*, 'TESSDARK', that is characterized by its compact, spreading, semi-pendulous plant habit, its floriferous plant habit, its flowers that are red-orange in color, its flowers with tepals that are wide and short, and its foliage that is dark green in color on the upper surface and red on the lower surface.

3 Drawing Sheets

Botanical classification: *Begonia* hybrid.
Cultivar designation: 'TESSDARK'.

RELATED APPLICATIONS

This application is related to U.S. Plant Patent applications filed for cultivars derived from the same breeding program entitled *Begonia* Plant named 'YASPWHIT' (U.S. Plant Pat. No. 23,281), *Begonia* Plant Named 'YASPMON' (U.S. Plant Pat. No. 20,846), *Begonia* Plant Named 'YASPRINK' (U.S. Plant Pat. No. 23,266), and *Begonia* Plant Named 'YASPED' (U.S. Plant Pat. No. 22,412).

BACKGROUND OF THE INVENTION

The present invention relates to a new and distinct cultivar of *Begonia* plant, botanically an interspecific hybrid that includes *Begonia boliviensis* hybrids in its parentage. The new cultivar is known as *Begonia* 'TESSDARK' and will be referred to hereafter by its cultivar name, 'TESSDARK'. 'TESSDARK' is a new cultivar of *Begonia* that is particular useful for use in flowerbeds, containers, and hanging baskets.

The new cultivar was derived from a controlled breeding program conducted by the inventor at his nursery in Congleton, Cheshire, United Kingdom. The overall purpose of the breeding program is to make unique selections of *Begonia* plants that perform well as basket and patio plants. 'TESSDARK' was selected in the Inventor's greenhouse in 2007 as a single unique plant from amongst the seedlings derived from a cross made in 2006 between unnamed *Begonia* plants of hybrid origin from the Inventor's breeding program as the female and male parents.

Asexual propagation of the new cultivar was first accomplished by stem tip cuttings in Congleton, Cheshire, United Kingdom in 2007 by the Inventor. Asexual propagation by stem tip cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'TESSDARK' as a new and distinct cultivar of *Begonia*.

1. 'TESSDARK' exhibits a compact, spreading, semi-pendulous plant habit.
2. 'TESSDARK' exhibits a floriferous blooming habit.
3. 'TESSDARK' exhibits flowers that are red-orange in color.
4. 'TESSDARK' exhibits flowers with tepals that are wide and short.
5. 'TESSDARK' exhibits foliage that is dark green in color on the upper surface and red on the lower surface.

The female parent of 'TESSDARK' differs from 'TESSDARK' in having flowers with tepals that are not as wide, in having a less vigorous growth rate, in having a more open plant habit, and in being less floriferous. The male parent differs from 'TESSDARK' in having leaves that are lighter green in color, in having flowers that are pale orange in color, in having a more mounded plant habit, and in being less floriferous. 'TESSDARK' can be most closely compared to cultivars from the same breeding program: 'YASPWHIT', 'YASPMON', 'YASPRINK', and 'YASPED'. 'YASPWHIT' differs from 'TESSDARK' in having white flowers lightly flushed with pink. 'YASPMON' differs from 'TESSDARK' in having flowers that are pink-orange in color and a more trailing plant habit. 'YASPRINK' differs from 'TESSDARK' in having pink flowers. 'YASPED' differs from 'TESSDARK' in having dark red flowers, a more pendulous plant habit and in having a more vigorous growth habit.

BRIEF DESCRIPTION OF THE DRAWINGS

The accompanying colored photograph illustrates the overall appearance and distinct characteristics of the new *Begonia*. The photographs were taken of 3 cuttings in a 15-cm container, approximately three months in age, as grown in an unheated greenhouse in Naadvijk, The Netherlands.

The photograph in FIG. 1 provides a view of the plant habit of 'TESSDARK' in bloom.

Figure 1:
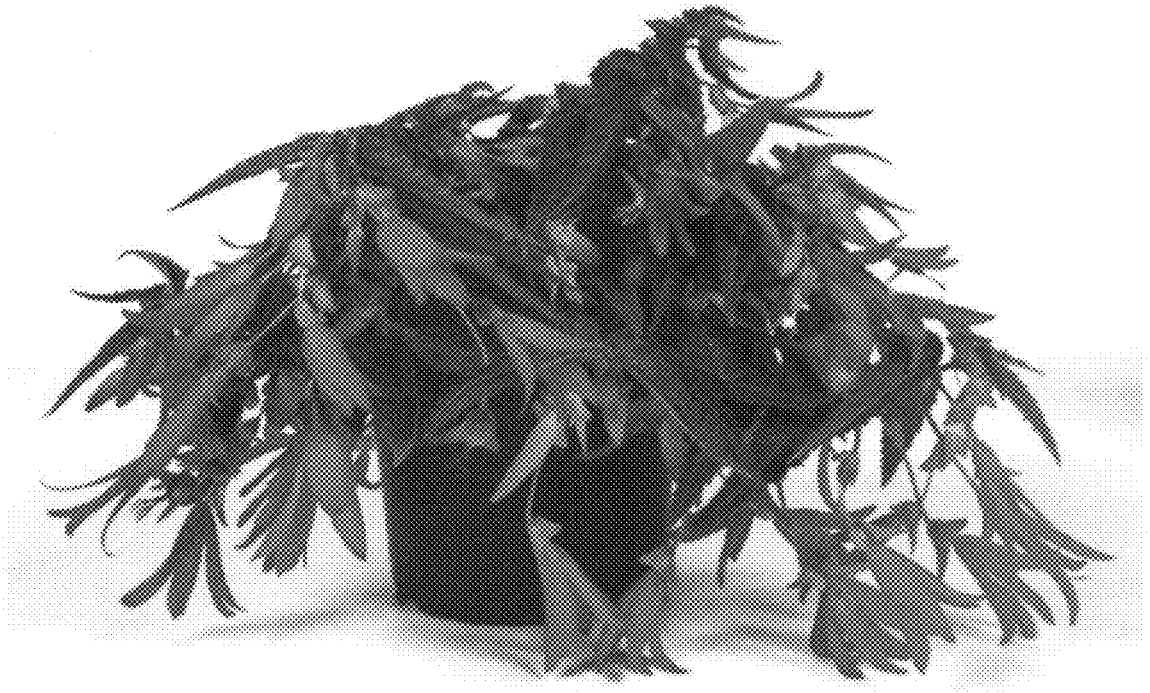
Figure 2:
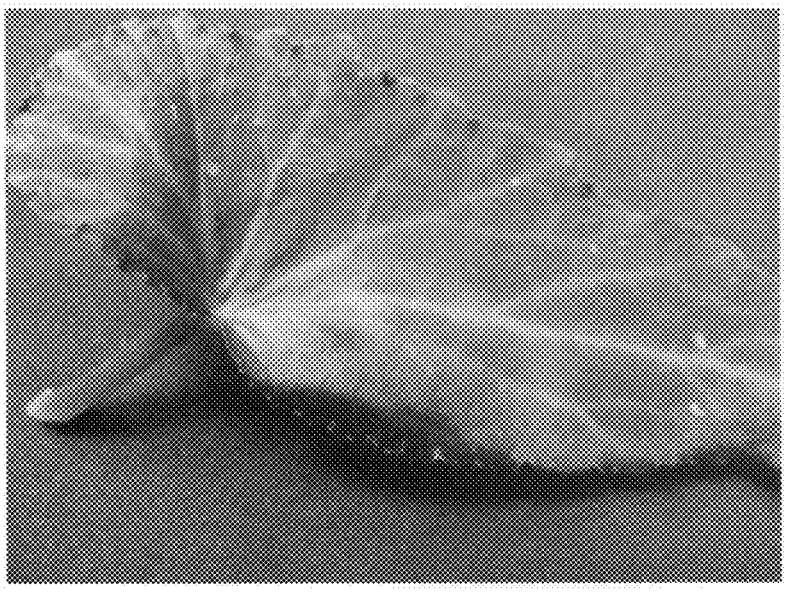

The photograph in FIG. 2 provides a close-up view of the upper surface of a leaf of 'TESSDARK'.

Figure 3:
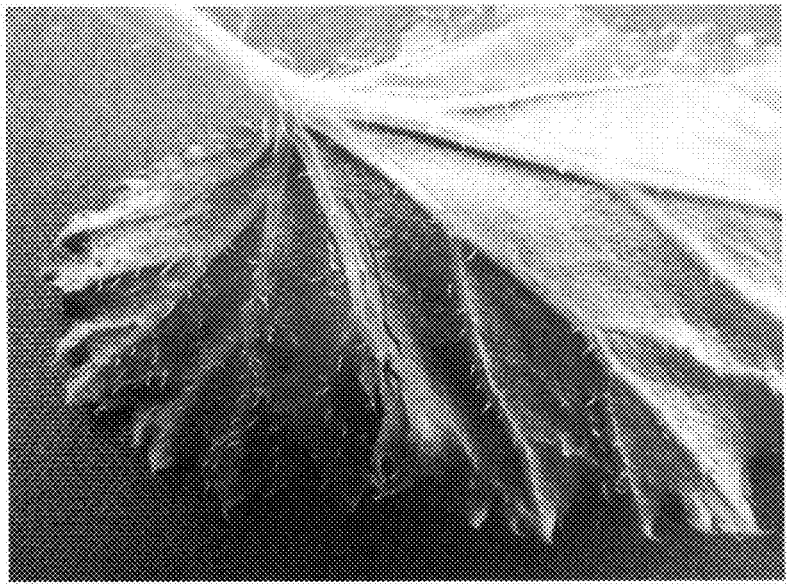

The photograph in FIG. 3 provides a close-up view of the lower surface of a leaf of 'TESSDARK'.

Figure 4:
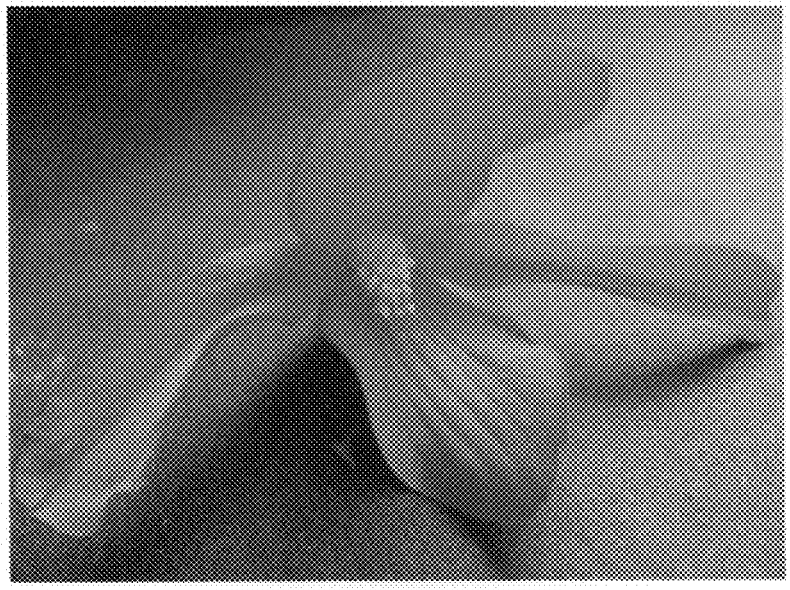

The photograph in FIG. 4 provides a close-up view of a male flower of 'TESSDARK'.

Figure 5:
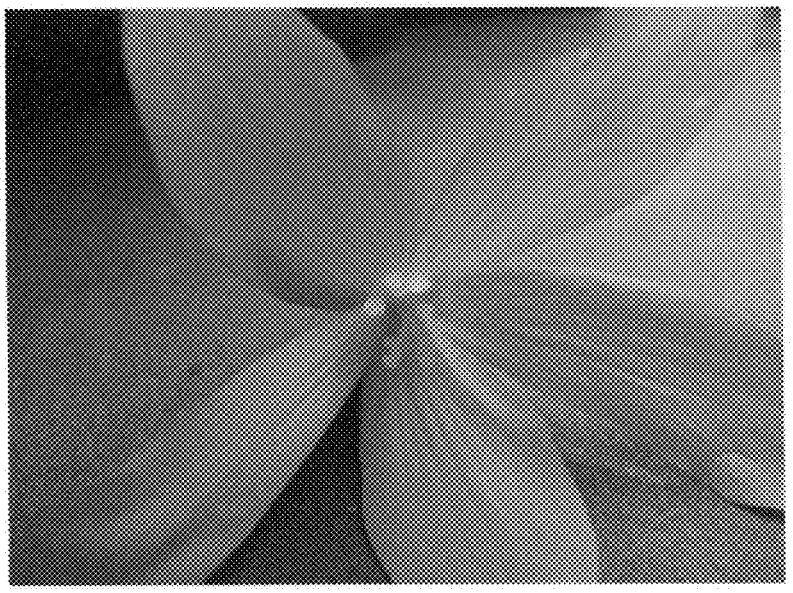

The photograph in FIG. 5 provides a close-up view of a female flower of 'TESSDARK'.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately three months in age grown in 15-cm containers (3 cuttings) under unheated greenhouse conditions in Naadvijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets and containers.

*Plant habit*.—Spreading.

*Flowering period*.—From May to October.

*Height and spread*.—Reaches about 25 cm in height and about 45 cm in spread.

*Cold hardiness*.—U.S.D.A. Zone 10.

*Diseases and pests*.—No susceptibility or resistance to diseases or pests has been observed.

*Root description*.—Fleshy to fibrous.

*Growth rate*.—Semi-vigorous.

*Propagation*.—Stem tip cuttings.

Stem description:

*Stem size*.—Average of 20 cm in length and 7 mm in diameter with lateral branches about 5 mm in diameter.

*Stem shape*.—Round, solid.

*Stem color*.—Ranging between 152B, 152C and 152D and 199C.

*Stem surface*.—Smooth, and covered with a few colorless hairs lenticels absent.

*Internode length*.—Up to 30 mm.

*Branching habit*.—Freely branching.

*Branching angle at emergence*.—Approximately 45° to horizontal.

Foliage description:

*Leaf shape*.—Lanceolate, strongly asymmetric with one side narrowly ovate and the other side is narrowly cordate and wider.

*Leaf division*.—Entire.

*Leaf base*.—Cordate.

*Leaf apex*.—Acuminate.

*Leaf venation*.—Pinnate, color 137C on upper surface and 138B on lower surface.

*Leaf margins*.—Irregular serrate with short bristles emerging from tips of the teeth.

*Leaf attachment*.—Petiolate.

*Leaf arrangement*.—Alternate.

*Leaf surface*.—Upper surface; slightly glossy and covered with very occasional scattered short colorless hairs, lower surface; slightly glossy and covered with very occasional scattered short colorless hairs mainly on midrib.

*Leaf color*.—Upper surface; N189A, lower surface; 184A to 185B.

*Leaf size*.—Average of 12.5 cm in length and 5 cm in width.

*Leaf fragrance*.—None.

*Petioles*.—Up to 3 cm in length and 3 mm in width, surface is sparsely pubescent with simple translucent hairs.

*Stipules*.—Narrowly triangular in shape, 145B to 145C and rapidly becoming dry and papery, about 6 mm in length and 3 mm in width.

Flower description:

*Inflorescence type*.—2 to 3 flowered cymes produced sequentially in the axils of the upper leaves, monoecious with single male and female flowers.

*Inflorescence number*.—Up to 10 per flowering stem.

*Peduncles*.—Up to 3.5 cm in length and 2 mm in width, color; 179A to 179B shading to 179D where less exposed.

*Flower persistence*.—Self-cleaning.

*Flower type*.—Single.

*Flower longevity*.—10 to 14 days depending on growing conditions.

*Flower fragrance*.—None.

*Flower number*.—3 per inflorescence, up to 12 per stem.

*Flower aspect*.—Horizontal.

*Bracts*.—2, rounded to reniform in shape, obtuse apex, up to 1 cm in length and 1.4 cm width, 145C to 145D, flushed with 34C towards the margins, covered with bristly hairs on margin.

Male flowers:

*Pedicels*.—Up to 2.4 cm in length and 1.5 mm in diameter, color; 43A on exposed side, 43C on shaded side.

*Flower buds*.—Flattened broad ovoid in shape, up to 3.3 cm in length and 1.5 cm in diameter, color is 40B.

*Flower size*.—Up to 4.6 cm in length and 7.4 cm in width.

*Flower shape*.—Flared to open.

*Flower aspect*.—Facing horizontally.

*Tepals*.—4 in number (2 inner and 2 outer), outer tepals; ovate in shape, obtuse apex, rounded base, average of 4.7 cm in length and 2.5 cm in width, glabrous and smooth surface, entire margin, color; outer surface is 40A to 43A, inner surface is 40A, inner tepals; narrow to ob-elliptic in shape, obtuse apex, cuneate base, up to 4.7 cm in length and 1.1 cm in width, surface is glabrous and smooth on both surfaces, entire margin, color; outer surface is 40A and 43A, inner surface is 40A.

*Perianth form*.—Flared, tepals are un-fused.

*Stamens*.—Numerous; connate below forming a tube, up to 1.2 cm in length and 2.5 mm in width, 10B in color.

*Filaments*.—Up to 4 cm in length, 0.5 mm in width, 10B in color.

*Anthers*.—Elliptic in shape, 1 mm in length, <1 mm in width and 11A in color.

*Pollen*.—Moderate in quantity and 10D in color.

Female flowers:

*Pedicels*.—Average 2.7 cm in length and 1.5 mm in width, 43A in color on exposed side, 43C in color on shaded side.

*Flower buds*.—Flattened ovoid in shape, about 2.7 cm in length and 1.5 cm in diameter, color is 40B.

*Flower size*.—About 4.2 cm in length (excluding ovary) and 5.5 cm in width.

*Flower shape*.—Flared to open.

*Flower aspect*.—Facing horizontally.

*Tepals*.—5 in number (3 inner and 2 outer), outer tepals; ovate to broad ovate in shape, acute to obtuse apex, rounded base, average of 3.9 cm in length and 1.2 cm in width, glabrous and smooth surface, entire margin, color; outer surface between 40A and 43A, inner surface is 40A, inner tepals; narrow ob-elliptic in shape, obtuse apex, narrow cuneate base, up to 3.9 cm in length and 1.9 cm in width, glabrous and smooth on both surfaces, entire margin, color; outer and inner surface is 40A.

*Perianth form*.—Flared, tepals are un-fused.

*Styles*.—3 in number, cylindrical, connate at base for <1 mm, up to 4 mm in length and 1 mm in diameter and 32B in color.

*Stigmas*.—Bifid in shape, stigmatic surfaces twisted around extensions of the style, lobes about 3 mm in length and 1 mm in diameter, 15C in color.

*Ovaries*.—Inferior, triangular in cross section with angles unequally winged, about 9 mm in length and 8 mm in width (excluding wings), color is 145C.

*Seed*.—Numerous, ovoid in shape, very small in size, color is 176A and <0.1 mm in diameter.

It is claimed:

1. A new and distinct cultivar of *Begonia* plant named 'TESSDARK' as herein illustrated and described.

* * * * *